(12) United States Patent
Daniel et al.

(10) Patent No.: US 11,491,284 B2
(45) Date of Patent: Nov. 8, 2022

(54) PLASMA TREATMENT METHOD FOR COATING A GLASS SYRINGE BODY FOR A HYPODERMIC PRE-FILLED GLASS SYRINGE

(71) Applicant: Gerresheimer Regensburg GmbH, Wackersdorf (DE)

(72) Inventors: Christian Daniel, Wernberg (DE); Lukas Baier, Regensburg (DE)

(73) Assignee: GERRESHEIMER REGENSBURG GMBH, Wackersdorf (DE)

(*) Notice: Subject to any disclaimer, the term of this patent is extended or adjusted under 35 U.S.C. 154(b) by 510 days.

(21) Appl. No.: 16/505,248

(22) Filed: Jul. 8, 2019

(65) Prior Publication Data

US 2020/0009329 A1 Jan. 9, 2020

(30) Foreign Application Priority Data

Jul. 9, 2018 (DE) .......................... 10 2018116560.9

(51) Int. Cl.
*B05D 3/04* (2006.01)
*B05D 3/14* (2006.01)
(Continued)

(52) U.S. Cl.
CPC .......... *A61M 5/343* (2013.01); *A61M 5/3129* (2013.01); *B05D 3/0493* (2013.01);
(Continued)

(58) Field of Classification Search
CPC ........ A61M 5/3129; A61M 2005/3131; B05D 3/0493; B05D 3/3145; B05D 7/227; B05D 2203/35
(Continued)

(56) References Cited

U.S. PATENT DOCUMENTS 4,767,414 A * 8/1988 Williams ................ A61M 5/31
604/230
8,747,962 B2 * 6/2014 Bicker .............. H01J 37/32082
118/723 R (Continued)

FOREIGN PATENT DOCUMENTS

DE 10 2005 040 266 A1 3/2007
DE 10 2008 033 939 A1 1/2010
(Continued)

OTHER PUBLICATIONS

Air (Synthetic & Compressed). Product description [online]. Linde Industrial Gases, 2013 [retrieved on Jan. 22, 2022]. Retrieved from the internet: <https://web.archive.org/web/20130120132840/http://www.linde-gas.com/en/products_and_supply/gases_atmospheric/air.html>. (Year: 2013).*

*Primary Examiner* — William P Fletcher, III
(74) *Attorney, Agent, or Firm* — Leydig, Voit & Mayer, Ltd.

(57) ABSTRACT

Method for coating a glass syringe body for a hypodermic pre-filled glass syringe, wherein at least one emulsion and/or one solution containing at least one layer-forming substance is applied to at least one inner surface of the hypodermic pre-filled glass syringe, which defines an axial direction, wherein at least a partial surface of the inner surface in a syringe cone of the pre-filled glass syringe is subsequently exposed to a plasma, wherein a negative pressure source is arranged in relation to the syringe cone in the axial direction opposite the atmospheric-pressure plasma source, wherein a negative pressure of less than atmospheric pressure is provided by means of the negative pressure source.

12 Claims, 5 Drawing Sheets

(51) Int. Cl.
  *B05D 7/22* (2006.01)
  *A61L 31/14* (2006.01)
  *A61M 5/34* (2006.01)
  *A61M 5/31* (2006.01)

(52) U.S. Cl.
  CPC ............ *B05D 3/145* (2013.01); *B05D 7/227* (2013.01); *A61L 31/14* (2013.01); *A61M 5/349* (2013.01); *A61M 2207/10* (2013.01); *B05D 2203/35* (2013.01)

(58) Field of Classification Search
  USPC ....... 427/488, 489, 508, 515, 535, 569, 578, 427/230, 238
  See application file for complete search history.

(56) References Cited

U.S. PATENT DOCUMENTS

| | | | | |
|---|---|---|---|---|
| 8,883,256 | B2* | 11/2014 | Pfuch | C23C 16/44 977/773 |
| 9,662,450 | B2* | 5/2017 | Jones | A61M 5/31 |
| 10,363,370 | B2* | 7/2019 | Weikart | C23C 16/045 |
| 10,953,431 | B2* | 3/2021 | Josten | C09J 5/02 |
| 2004/0231926 | A1* | 11/2004 | Sakhrani | B05D 3/145 184/18 |
| 2005/0101916 | A1* | 5/2005 | Brandhorst | A61M 5/3129 604/187 |
| 2009/0155490 | A1* | 6/2009 | Bicker | H01J 37/32082 118/723 R |
| 2009/0181185 | A1* | 7/2009 | Grosse | B05D 1/62 118/723 MP |
| 2012/0171386 | A1* | 7/2012 | Bicker | B05D 3/141 427/488 |
| 2014/0010969 | A1* | 1/2014 | Bicker | H01J 37/32394 427/535 |

FOREIGN PATENT DOCUMENTS

| | | |
|---|---|---|
| DE | 10 2017 212 974 A1 | 1/2019 |
| EP | 1 352 667 A1 | 10/2003 |

* cited by examiner

PLASMA TREATMENT METHOD FOR COATING A GLASS SYRINGE BODY FOR A HYPODERMIC PRE-FILLED GLASS SYRINGE

CROSS-REFERENCE TO RELATED APPLICATIONS

This application is a U.S. Nonprovisional Application filed under 35 U.S.C. §111(a) which claims the benefit of Germany Application No. 10 2018 116 560.9, filed Jul. 9, 2018. This application is hereby incorporated by reference in its entirety.

BACKGROUND OF THE INVENTION

The present invention relates to a method for coating a glass syringe body for a hypodermic pre-filled glass syringe. The present invention further relates to a hypodermic pre-filled glass syringe. Furthermore, the present invention also relates to a plasma treatment device for glass syringe bodies of hypodermic pre-filled glass syringes.

Hypodermic pre-filled glass syringes are generally intended for use on the skin of a patient, in particular for penetrating to the hypodermis thereof. Such generic syringes typically comprise an elongated cylindrical sleeve having two diametrically opposite ends and a chamber formed between the two ends for storing a substance, for example a fluid, preferably with an active substance. The one of the two ends has an opening for ensuring the insertion of a plunger and optionally a flange for actuation with the fingers by a user. The other of the two ends generally tapers in cross-section in order to form a syringe cone and is substantially closed except for a narrow passage, or end channel, extending from the sleeve chamber through the syringe cone and allowing the substance to escape, or be pushed, from the chamber through the syringe cone. A cannula may be attached to the syringe cone end, wherein the cannula can, for example, be attached within the passage by means of an adhesive. Alternatively, the cannula may also be attached to the sleeve body from outside by means of a cannula holder. In this case, the cannula is generally understood to be a hollow needle which is used to penetrate into human or animal tissue in order to inject the fluid or remove body fluids with the aid of the syringe.

It is known to provide a glass syringe with a lubricant layer, such as a silicone layer, on the inner side in order to firstly achieve a reduction in the friction between the plunger and the sleeve body inner surface for easier movement of the plunger in relation to the sleeve body and to secondly simply ensure a completely circumferential sealing contact surface between the hard glass body inner side and the hard plunger outer side due to the deformability of the lubricant layer. Two possibilities basically exist in this respect. On the one hand, the glass syringe can be coated with a lubricant layer in the interior, wherein oily silicon is used, for example. In this case, the cannula is glued in prior to the coating with the lubricant layer. A further possibility is bake-on siliconization, which is used in particular if a harder adhesion of the silicone oil to the syringe is required. In this connection, baking is to be understood as curing. In this technique, it is however not possible to glue the cannula prior to siliconization since the cannula does not withstand the high temperatures that occur during bake-on siliconization. The problem previously unsolved in the field of glass syringes provided with a lubricant inner layer, in particular in the case of bake-on-siliconized glass syringes, of adhering a cannula with sufficient adhesion and strength properties in the end channel of the glass syringe thus exists. It was found that sufficient adhesion between adhesive and glass cannot be built up due to the presence of the silicone layer.

One solution to this problem is to render a silicone layer adhesive by using an atmospheric plasma to pretreat the adhesive layer. However, it is not possible, in particular on account of the dimensional nature of the glass syringe, to bring about complete access of the plasma to the lubricant layer, above all in the region of the end-side inner channel, in order to thus realize reliable adhesion of the cannula in the end channel.

EP 1 352 667, for example, discloses a method for producing an injection syringe in which a syringe body is provided with a lubricant in the interior at a high temperature. At the joint between the syringe body and the cannula, the lubricant is subsequently removed, for example by means of plasma treatment, in order to enable adhesion of the adhesive used for joining to the syringe body inner surface and thus an adhesion of the cannula to the syringe body. This known method has the disadvantage that the complete removal of the lubricant in the spatially tightly limited region at the tip of the sleeve body can only be achieved with great effort.

SUMMARY OF THE INVENTION

It is therefore an object of the invention to overcome the disadvantages from the known prior art, in particular to provide a method for coating a glass syringe body, in particular a siliconized or bake-on-siliconized glass syringe body, provided with a lubricant inner layer for a hypodermic pre-filled glass syringe, in which the holding force between the cannula and the glass syringe body is increased, in particular to achieve holding forces in accordance with DIN ISO 7864, and in which the narrow end channel of the glass syringe can be subjected to an improved treatment with atmospheric plasma. It is furthermore an object of the present invention to provide a hypodermic pre-filled glass syringe which has an increased holding force between the glass syringe and the cannula and is subjected to improved treatment with atmospheric plasma. Furthermore, it is an object of the present invention to provide a plasma treatment device for a glass syringe body of a hypodermic pre-filled glass syringe, with which device an increased holding force between the cannula and the glass syringe body can be achieved and improved treatment with atmospheric plasma can be carried out.

This object is achieved by the features of claims 1, 9, 11 and 15, respectively.

Accordingly, a method for coating a glass syringe body for a hypodermic pre-filled glass syringe is proposed, wherein at least one emulsion and/or one solution containing at least one layer-forming substance is applied to at least one inner surface of the hypodermic pre-filled glass syringe. The pre-filled glass syringe defines an axial direction which runs substantially in parallel to a longitudinal extent direction of the pre-filled glass syringe. The hypodermic pre-filled glass syringe may be made of plastic, a metal or an alloy. The hypodermic pre-filled glass syringe may have a flat or curved inner surface. The hypodermic glass syringe may in particular initially be a semifinished product, which is processed further into a finished product in subsequent method steps. In other embodiments of the invention, the hypodermic glass syringe can also be formed as a finished product, which no longer requires further processing after carrying out the proposed coating method.

The coating contains at least one layer-forming substance which is present in the form of an emulsion and/or a solution. In addition to the layer-forming substance, the emulsion or the solution contains at least one solvent. For the purposes of the present description, the carrier matrix of an emulsion is also called a solvent, even if the layer-forming substances are only emulsified and are not dissolved in the stricter sense.

The emulsion or the solution can be applied to at least one inner surface of the hypodermic pre-filled glass syringe by methods known per se. For example, a full coating of the hypodermic pre-filled glass syringe can also be provided, i.e. the entire inner surface of the hypodermic pre-filled glass syringe is coated. The emulsion or solution can be applied, for example, by spraying, printing, painting or dipping. In order to make possible a more uniform coating with the emulsion or the solution, additional measures can be taken, for example lowering the viscosity by heating and/or dilution or supporting the coating by electric fields, such as in the case of electrophoretic coating.

The hypodermic pre-filled glass syringe can be heat-treated after the application of the emulsion or the solution. The heat treatment can take place immediately after the application of the emulsion or of the solution. For example, the heat treatment may be performed after a preceding drying step. On the one hand, the heat treatment leads to the solvent of the emulsion or of the solution being evaporated or expelled from the layer. In addition, a bond can be established between the layer-forming substances and the inner surface of the hypodermic pre-filled glass syringe, for example by covalent bonds or van der Waals bonds, which bring about hardening of the layer. In some embodiments of the invention, the layer-forming substances may also be crosslinked to one another and form, for example, a polymer or a polymer-like compound. In an exemplary embodiment of the invention, the coating produced in this way is hydrophobic and/or has improved sliding properties in comparison to the untreated surface. Preferably, the coating produced can also be chemically inert to gases or liquids with which the hypodermic pre-filled glass syringe comes into contact during intended use.

According to the invention, at least one partial surface of the inner surface of the hypodermic pre-filled glass syringe provided with the coating is subjected to a plasma treatment in a subsequent method step. For example, the partial surface is an inner surface in a syringe cone of the pre-filled glass syringe. As a result, the effects of the coating can be at least partially deactivated or reversed without completely removing the coating as such. In the context of the present description, a plasma is understood to mean a partially ionized gas which acts on at least one partial surface of the coating at a predeterminable pressure and with a predeterminable composition for a specific period of time. In an exemplary embodiment of the invention, the partial surface may be as large as the coated inner surface, whereby the plasma acts on the entire previously applied coating on the inner surface. If the coated inner surface comprises the entire inner surface of the hypodermic pre-filled glass syringe, the plasma can also act on the entire inner surface of the hypodermic pre-filled glass syringe. According to another exemplary embodiment of the invention, only a portion of the coating is subjected to the plasma treatment, whereas at least a further portion of the coating is not exposed to the plasma. For example, the partial surfaces, such as the partial surface in the syringe cone of the pre-filled glass syringe, that are to form a joint in a subsequent method step can be subjected to the plasma treatment in order to in this way improve the adhesion of adhesives or solder or to make them possible in the first place. The plasma is generated, for example, by an atmospheric-pressure plasma source which is positioned in front of one end of the syringe cone when viewed in the axial direction in order to introduce the plasma into the syringe interior via an end channel or a passage formed in the syringe cone.

A negative pressure source is arranged in relation to the syringe cone in the axial direction opposite the atmospheric-pressure plasma source, wherein a negative pressure of less than atmospheric pressure is provided in the syringe interior, preferably in the syringe cone interior, in particular in a section of the syringe cone interior, by means of the negative pressure source. According to one exemplary embodiment, a vacuum is applied as the negative pressure. The application of negative pressure in the syringe interior allows the plasma as such to penetrate and the penetration depth of the plasma into the syringe cone to be increased, as a result of which a considerably larger surface, which is in particular subsequently used as an adhesive surface for the cannula or injection needle, can be treated by means of the atmospheric-pressure plasma source. As a result of the enlargement of the surface treated by plasma, the holding forces between the cannula and the glass syringe can be increased considerably, wherein in particular the adhesion between the adhesive and the glass is significantly increased, which preferably makes it possible to achieve holding forces in accordance with DIN ISO 7864. Furthermore, arranging the negative pressure shaft for providing negative pressure in the syringe interior provides advantageous surface activation for subsequent gluing. Moreover, other undesired particles, such as dust or dirt, can also be removed from the syringe interior in order to obtain a surface that is as clean as possible, i.e. free of foreign particles. This in turn can achieve better adhesion of the adhesive to the glass body inner surface.

According to a preferred embodiment of the present invention, a suction mandrel of the negative pressure source is inserted into the glass syringe body interior, preferably into a plunger chamber of the glass syringe body. The plunger chamber is to be understood as the volume which is bounded from outside by the glass syringe itself and into which a plunger for displacing substance arranged in the plunger chamber, such as a liquid, preferably with an active substance, can be inserted from outside, in particular in the axial direction, from the side of the glass syringe opposite the atmospheric-pressure plasma source. Via this suction mandrel, which is adapted by dimensioning to an inner diameter of the glass syringe body, a negative pressure of desired magnitude can be generated in the glass body interior, preferably in the syringe cone, preferably in a section of the syringe cone, in a targeted manner according to the requirement.

According to a development of the present invention, the suction mandrel is brought into a preferably sealing contact with an inner side and/or a bottom surface of the plunger chamber. For example, the suction mandrel can be dimensioned with respect to the inner diameter of the glass syringe, in particular the plunger chamber of the glass syringe, such that a fully circumferential contact between the suction mandrel and the glass syringe inner surface exists at least partially when viewed in the axial direction. Alternatively or additionally, it is conceivable to provide sealing means, such as a sealing ring or a sealing hose, in order to produce the sealing contact between the glass syringe inner surface and the suction mandrel. The sealing means, in particular the sealing ring, is preferably located at a front end of the suction mandrel facing the atmospheric-pressure plasma source.

In an exemplary embodiment of the invention, the action of the plasma reduces the carbon content of the coating to less than about 80% or less than about 75% or less than about 70% or less than about 60% of the initial value prior to the plasma treatment. The reduction in carbon content can also have the effect that the bonds within the coating change. For example, the coating may be converted from a polymeric structure to a glassy or amorphous structure. Alternatively or additionally, the action of the plasma can reduce the layer thickness in the treated partial surface. In another exemplary embodiment of the invention, the layer thickness may be reduced by more than about 20% or more than about 25% or more than about 30%. It was found that the action of the plasma does not completely remove or does not have to completely remove the coating. Rather, a layer thickness of more than about 70% or more than about 60% or more than about 50% of the layer thickness applied in the first method step may remain in the partial surface after the plasma treatment.

It was also found that the plasma treatment can alter the bonding conditions and/or the layer thickness and/or the element inventory of the originally applied coating in the partial surface exposed to the plasma. For example, roughening of the coating and/or hydrophilicization can be achieved so that a subsequent coating or joining method can be facilitated or made possible in the first place. Furthermore, the plasma treatment can be easier to carry out than a complete removal of the coating, which adheres very strongly to the inner surface of the hypodermic pre-filled glass syringe in some circumstances and can only be removed mechanically or wet-chemically, wherein on the one hand the resulting environmental load can be avoided according to the invention and on the other hand expensive measures for restricting the access of a liquid or gaseous etching medium outside the partial surface to be treated can be avoided.

In an exemplary embodiment of the invention, the layer thickness of the coating in at least the partial surface before the action of the plasma is between about 20 nm and about 100 nm or between about 30 nm and about 70 nm. Such a coating does not impair the dimensional accuracy of the coated inner surface of the hypodermic pre-filled glass syringe but may already be sufficient to bring about improved sliding properties, hydrophobization and/or passivation of the surface.

According to a development of the invention, the emulsion and/or the solution may contain or consist of at least one silicone oil and a solvent; for example, the solvent may be water or contain water or contain aliphatic hydrocarbons or aromatics, such as hexane, heptane, toluene and/or xylene. It is lastly also conceivable that the solvent also contains an alcohol and/or glycerol and/or ether in order to form an emulsion. A further exemplary embodiment of the solvent consists in that it is evaporated or expelled from the resulting coating either under normal ambient conditions or at elevated temperature in the heating cabinet or oven so that a coating which contains or consists of silicone remains on the inner surface or on a partial surface of the coated inner surface of the hypodermic pre-filled glass syringe.

In an exemplary embodiment, the coating may contain at least carbon and oxygen and hydrogen and silicon. Furthermore, the coating may contain or consist of at least one poly-organo-siloxane. Through the action of the plasma, the carbon can be removed from the coating at least partially so that the coating contains or consists of silicon oxide and/or silicon nitride and/or silicon oxynitride after the plasma treatment.

In a further exemplary embodiment, the partial surface of the inner surface before the plasma treatment is hydrophobic; the partial surface of the inner surface may be hydrophilic before the plasma treatment and hydrophobic after the plasma treatment. For the purposes of the present description, a hydrophobic coating is understood to mean a surface which, upon contact with water, forms a contact angle of more than 90°. For purposes of the present description, a hydrophilic surface is a surface which, when wetted with water, forms a contact angle of less than 90°. The surface energy can therefore be changed by the plasma treatment to such an extent that the adhesive strength or wettability with a lubricant, an adhesive, a solder or a lacquer is increased or made possible in the first place.

The plasma may contain or consist of an active gas, for example. The active gas preferably contains or consists of nitrogen and/or oxygen or synthetic air or atmospheric air, for example.

In another exemplary embodiment of the invention, the plasma may act for about 0.4 to about 5 seconds or for about 0.5 to about 4 seconds or for about 0.5 to about 1.5 seconds or for about 5 to about 60 seconds. It was found that this short treatment time is already sufficient to convert a hydrophobic silicone coating into a hydrophilic, silicon-containing compound so that the method according to the present invention can also be used economically in the production of mass products.

In a development of the invention, an atmospheric-pressure plasma produced with a dielectrically impeded discharge can be used. In this way, the method can be easily integrated into existing production processes. On the one hand, this is associated with the fact that the use of a dielectrically impeded discharge ensures that the electrical power coupled into the plasma remains limited. On the other hand, thermal damage and/or damage of the coating of the hypodermic pre-filled glass syringe can be avoided.

In an exemplary embodiment of the invention, a turbulent flow of the working gas can be used to generate the plasma. The discharge can be lengthened thereby. The treatment of the inner surfaces of cylindrical hollow bodies in particular enhances this effect since the surfaces present there support the discharge. Slim objects, such as syringes, in particular the syringe cone, can thus be treated more easily or can thus be treated in the first place.

In an exemplary embodiment of the invention, the plasma may contain or consist of an inert gas. The inert gas can preferably be or contain a noble gas. It is also possible for the plasma to contain or consist of argon. An inert gas plasma in particular ensures that the components of the coating are not oxidized or reduced or otherwise react with the process gas of the plasma, so that the coating does not react undesirably or is not removed from the surface by reactive etching.

In a development of the present invention, the plasma can be generated by an alternating voltage or a pulsed voltage having a frequency between about 10 kHz and about 30 kHz or between about 15 kHz and about 25 kHz.

According to an exemplary embodiment of the invention, a plasma beam generated by an electric field between the surface of the component and at least one counter electrode by ionizing a working gas stream may be used. It is also possible to use a plasma jet, wherein the plasma is generated in the interior of the plasma source by electric fields or electromagnetic radiation and is expelled from the source by the working gas stream. In exemplary embodiments of the invention, the plasma is generated with a dielectrically impeded discharge. Plasmas produced in this way only have low temperature increases of less than about 50 K or less than about 30 K in relation to the environment so that thermal damage can be avoided even in the case of sensitive surfaces. This is, for example, helpful in the treatment of components made of a polymer or other plastics.

In a development of the present invention, the plasma is generated as a plasma beam or plasma jet, which acts at least on the partial surface of the inner surface of the syringe cone. It may furthermore be provided that the plasma acts in particular only when the negative pressure is provided by the negative pressure source.

According to a further aspect of the present invention which can be combined with the previous aspects, the injection needle is connected to the glass syringe body along a joint in a method for producing a hypodermic pre-filled glass syringe with a glass syringe body, which is coated according to the coating method according to the invention described above, and an injection needle which are joined to one another. In this case, the joint can comprise the partial surface in the syringe cone of the pre-filled glass syringe. The coating or treatment method according to the invention, by arranging an atmospheric-pressure plasma source and a negative pressure source on the pre-filled glass syringe in such a way that the partial surface comprised by the joint is coated or treated prior to the joining of the injection needle and the glass syringe body, brings about the advantages of the pre-filled glass syringe according to the invention and described above, in particular increased needle holding forces in the syringe body axial direction and/or in particular increased adhesion of the adhesive to the glass syringe body.

In a development of the present invention, the joining can be carried out using an adhesive which is selected in particular from an acrylate and/or polyurethane and/or an epoxy resin and/or a cyanoacrylate. Such adhesives have high adhesive strengths with simple processability and high initial strengths so that rapid production is made possible.

According to another aspect of the present invention, which can be combined with the previous aspects, a hypodermic pre-filled glass syringe comprises a glass syringe body and an injection needle which are connected to each other by an adhesive layer along a joint. The joint preferably comprises at least one partial surface of an inner surface of a syringe cone of the glass syringe body. The adhesive layer between the joint and the injection needle provides a needle holding force in the axial direction in order to ensure that the injection needle remains adhered to the joint during application of the pre-filled glass syringe. According to the invention, at least one atmospheric-plasma-treated coating is applied to the inner surface of the syringe cone. The needle holding force is preferably at least (a) 11 N for needle diameters less than 0.33 mm,
(b) 22 N for needle diameters less than 0.55 mm,
(c) 34 N for needle diameters less than 0.7 mm,
(d) 40 N for needle diameters less than 0.8 mm,
(e) 44 N for needle diameters less than 0.9 mm,
(f) 54 N for needle diameters less than 1.1 mm, and/or
(g) 44 N for needle diameters greater than or equal to 1.1 mm.

The holding forces thereby achieved are sufficient to ensure the strength requirements according to DIN ISO 7864 and thus to achieve sufficient adhesion between the injection needle and the glass syringe body.

According to one exemplary embodiment of the invention, the layer thickness of the coating in at least the partial surface of the inner surface before the action of the plasma is between about 20 nm and about 100 nm or between about 30 nm and about 70 nm. By the plasma treatment in the partial surface of the inner surface, the layer thickness of the coating can decrease by more than about 20% or more than about 25% or more than about 30%. Alternatively or additionally, a layer thickness of more than about 70% or more than about 60% or more than about 50% may remain after the plasma treatment of the partial surface.

According to another aspect of the present invention, the coating may contain at least carbon and oxygen and hydrogen and silicon. Alternatively or additionally, the coating may contain at least one poly(-organo)-siloxane. The carbon content of the coating is preferably reduced to less than about 80% or less than about 75% or less than about 70% or less than about 60% of the initial value prior to the plasma treatment.

In a further exemplary embodiment of the pre-filled glass syringe according to the invention, the adhesive is selected from an acrylate and/or a polyurethane and/or an epoxy resin and/or a cyanoacrylate.

According to another aspect of the present invention, which can be combined with the previous aspects, a plasma treatment device for glass syringe bodies of hypodermic glass syringes comprises an atmospheric-pressure plasma source for providing plasma for treating an inner surface of a syringe cone of the glass syringe body. The glass syringe body is preferably a glass syringe body that is previously coated by means of a lubricant layer, such as a silicone layer. For example, the glass syringe body may also have been bake-on-siliconized. The effect of the coating can be at least partially deactivated or reversed by the plasma treatment without completely removing the coating as such. As a result of the plasma treatment, the respective surface, i.e. a glass body inner surface, is treated in such a way that the adhesive strength or the wettability with a lubricant, an adhesive, a solder or a lacquer is increased or made possible in the first place.

The plasma treatment device furthermore comprises a negative pressure source for providing a negative pressure less than atmospheric pressure. For example, a vacuum may be generated. According to the invention, the atmospheric-pressure plasma source and the negative pressure source are or can be arranged opposite each other in relation to the syringe cone. In particular, the atmospheric-pressure plasma source is arranged on the side of the syringe cone on which the liquid accommodated inside the syringe leaves the syringe, and the negative pressure source is arranged on the side of the syringe via which the syringe is filled with the liquid. The provision of the negative pressure source allows the plasma as such to penetrate and the penetration depth into the syringe cone to be increased. This enables a defined treatment of the syringe cone interior with pure atmospheric plasma. Consequently, an increase in the adhesion of adhesive and glass can be achieved, whereby an increased holding force between the injection needle or cannula to be attached and the glass syringe is achieved. In addition, the provision of negative pressure also brings about a sealing effect since the plasma is prevented from passing into the syringe body during the treatment of the syringe body and resulting there in an undesired treatment of further regions of the syringe body interior.

In an exemplary embodiment of the present invention, the negative pressure source of the plasma treatment device comprises a suction mandrel, the outer diameter of which is smaller than or equal to a plunger chamber inner diameter of the glass syringe body, in particular of the plunger chamber.

The suction mandrel serves, for example, for the targeted application of negative pressure and can preferably be designed in such a way that a magnitude or level of the negative pressure can be regulated or adjusted via said suction mandrel.

In a further exemplary embodiment of the plasma treatment device according to the invention, the suction mandrel has an insertion length along which the outer diameter is smaller than the plunger chamber inner diameter of the glass syringe body. The insertion length is measured in the axial direction, for example. The insertion length can be at least as long as the cylinder height of the plunger chamber. The plasma treatment device may also be designed to introduce the suction mandrel into the plunger chamber of the glass syringe body in order to apply a negative pressure there. The suction mandrel can preferably be introduced into the plunger chamber up to contact with a bottom surface of the plunger chamber. In addition, a sealing effect can thereby be achieved between the glass body inner surface, in particular the bottom surface, and the suction mandrel in order to in particular prevent plasma from entering the syringe body during the treatment.

According to a development of the present invention, the suction mandrel has a sealing means, such as a sealing ring and/or a sealing hose. The sealing means is arranged, for example, at the front end, which faces in the direction of the syringe cone when viewed in the axial direction. The sealing means is in particular provided to be brought into contact with an inner diameter, i.e. a plunger chamber inner surface, and/or a bottom surface of the plunger chamber.

BRIEF DESCRIPTION OF THE DRAWINGS

Other properties, features and advantages of the invention become apparent below from the description of preferred embodiments of the invention with reference to the accompanying exemplary drawings, which show.

DETAILED DESCRIPTION OF THE INVENTION

Figure 1:
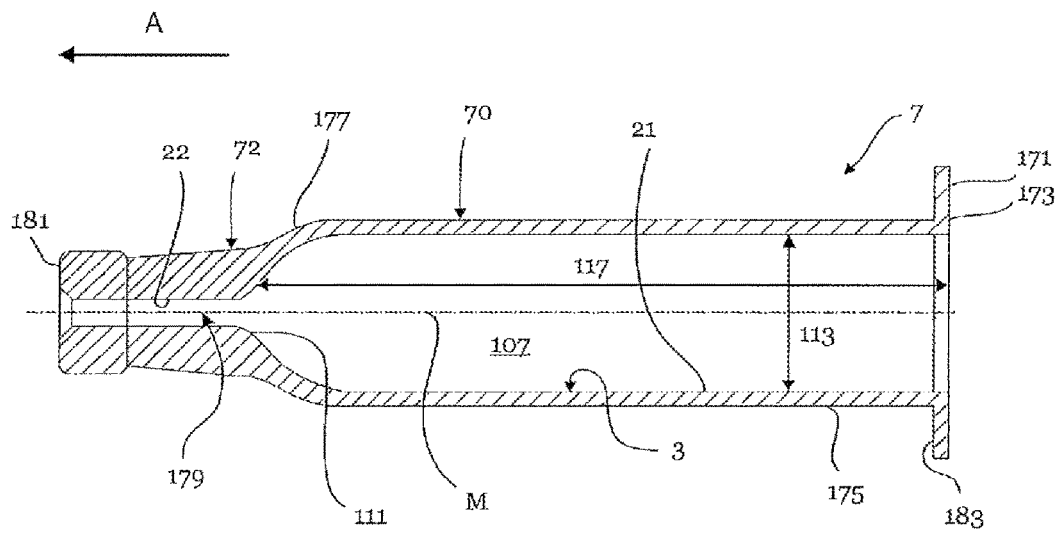
FIG. 1 a cross-sectional view of a hypodermic pre-filled glass syringe according to the invention.

In the following illustrations of preferred embodiments, the same or similar reference numerals are used for the same or similar components. A hypodermic pre-filled glass syringe according to the invention is generally provided with reference numeral 7. A plasma treatment device according to the invention for glass syringe bodies of hypodermic production syringes is generally provided with reference numeral 100.

FIG. 1 schematically shows a hypodermic pre-filled glass syringe 7 according to the invention in a sectional view, wherein a glass syringe body 70 of the pre-filled glass syringe 7 is shown hatched. The glass syringe 7 or the glass syringe body 70 substantially comprises a flange section 171 at an end 173 when viewed in the axial direction A, an elongated plunger section 175 which has a substantially constant cross-section and a constant wall thickness and which adjoins the flange section 171 when viewed in the axial direction A, and a syringe cone 72 which has a tapering cross-section and is formed with a thicker wall thickness and into which the plunger section 175 opens in the axial direction A. On the inside, the plunger section 175 limits or defines a plunger chamber 107. The syringe cone 72 is adjoined by a funnel section 177 of the plunger section 175 in the interior of which the plunger volume 107 tapers in a funnel-like manner. Through the syringe cone 72, a passage 179 extends substantially in the axial direction A from a syringe cone end 181 opposite the flange end 173 to the plunger chamber 107. The passage or end channel 179 has a substantially constant cross-section during its course. At the syringe cone end 181, the passage 179 may be chamfered, for example with a chamfer at an angle of 45° with respect to the axial direction A in order to facilitate later insertion of a cannula or injection needle and/or an atmospheric-pressure plasma source 101 described in detail below. FIG. 1 indicates a center line or line of symmetry M by a dash-dot line oriented substantially in parallel to the axial direction A. It can be seen that the pre-filled glass syringe 7 is designed to be symmetrical with respect to the center line M. On the inside, i.e. on an inner surface 21 of the pre-filled glass syringe 7, a coating 3 which is preferably designed as a bake-on siliconization is applied. This in particular ensures that a plunger 71, which is to be inserted and is described in more detail below, can be pushed with respect to the inner surface 21 of the glass syringe 7 with as little friction as possible and thus in an easily sliding manner. A partial surface 22 of the inner surface 21, which, as can be seen in particular in FIG. 1, forms at least a part of the syringe cone inner surface or the inner surface of the passage 179, is provided frontally as a later adhesive surface for the injection needle 73 or cannula 76 to be glued in. It is clear that the partial surface 22 is also treated with the coating 3 by the atmospheric-pressure plasma source 101. Furthermore, it is preferably the partial surface 22 which is treated with the negative pressure source 103 using the coating method according to the invention in order to treat the partial surface 22 in such a way that an increased adhesion of the adhesive used for gluing is achieved. The treatment of the syringe interior with the atmospheric-pressure plasma source 101 and the negative pressure source 103 is described in more detail with reference to FIGS. 2 to 4.

The flange section 171 has at least one flange web 183 which extends at least partially in the circumferential direction and extends away from the center axis M perpendicularly to the axial direction and which is provided for actuation with the fingers by a user.

Figure 2:
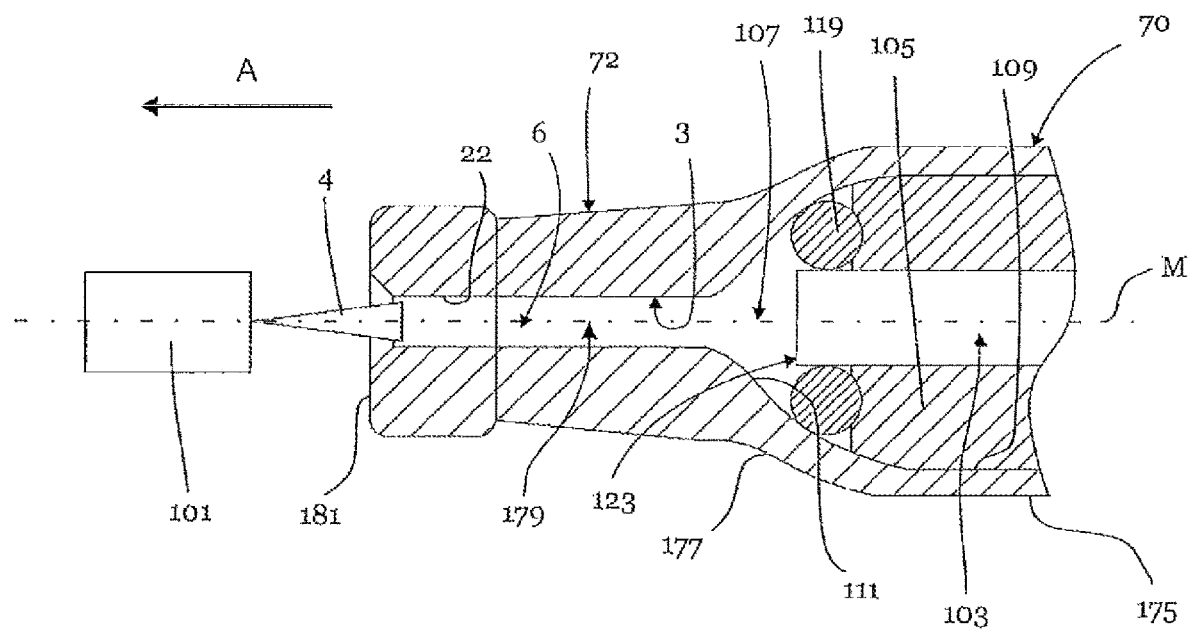
FIG. 2 a partial cross-sectional view of a hypodermic pre-filled glass syringe according to the invention with plasma source and negative pressure source.

FIG. 2 schematically illustrates a section of a pre-filled glass syringe 7 according to the invention, wherein an atmospheric-pressure plasma source 101 is arranged on the syringe-cone-side end 181 and a negative pressure source 103 is located on the plunger-section side in the interior of the plunger chamber 107. With regard to the details regarding a preferred embodiment of the atmospheric-pressure plasma source 101, reference is made to FIG. 5. In FIG. 2, this source is shown merely as a block, which schematically indicates that a plasma beam 4 is introduced via the syringe-cone-side end 181 into the end channel 179 in the syringe cone 72 in order to treat the inner surface 21 and the partial surface 22 with the plasma beam 4. The plasma treatment of the inner surfaces of the pre-filled glass syringe 7 is combined according to the invention with the application of a negative pressure source 103 preferably in the syringe interior. Of the negative pressure source 103, only a suction mandrel 105 introduced into the plunger chamber 107 of the glass syringe body 70 is shown in FIG. 2. In the illustrated position of the suction mandrel 105 with respect to the glass syringe body 70, the suction mandrel 105 is in contact with an inner side 109 of the glass syringe body 70, which contact is a sliding contact in this case, and a rudimentarily funnel-shaped bottom surface 111 of the plunger chamber 107 which prevents further insertion of the suction mandrel 105 into the plunger chamber 107. According to the embodiment in FIG. 2, a sealing ring 119 is arranged on a front end 123 of the suction mandrel 105 facing in the axial direction A in the direction of the bottom surface 111 in order to in particular provide a sealing contact with the bottom surface 111. Alternatively or in addition to the sealing ring 119, a sealing hose (not shown) for providing an additional sealing effect can also be attached to the suction mandrel. It can be seen that negative pressure of less than atmospheric pressure is generated by the negative pressure source 103 or by the suction mandrel 105 of the negative pressure source 103 in the region of the syringe cone 72, i.e. substantially in the passage 179, in order to apply both atmospheric-pressure plasma and negative pressure to the partial surface 22 of the inner surface 21 of the pre-filled glass syringe 7. As a result, the advantageous property change according to the invention arises on the partial surface 22 in order to facilitate or enhance the subsequent gluing-in of the injection needle 73 or of the cannula 76 and to increase the holding force with respect to the glass body inner side 22 in the axial direction A.

Figure 3:
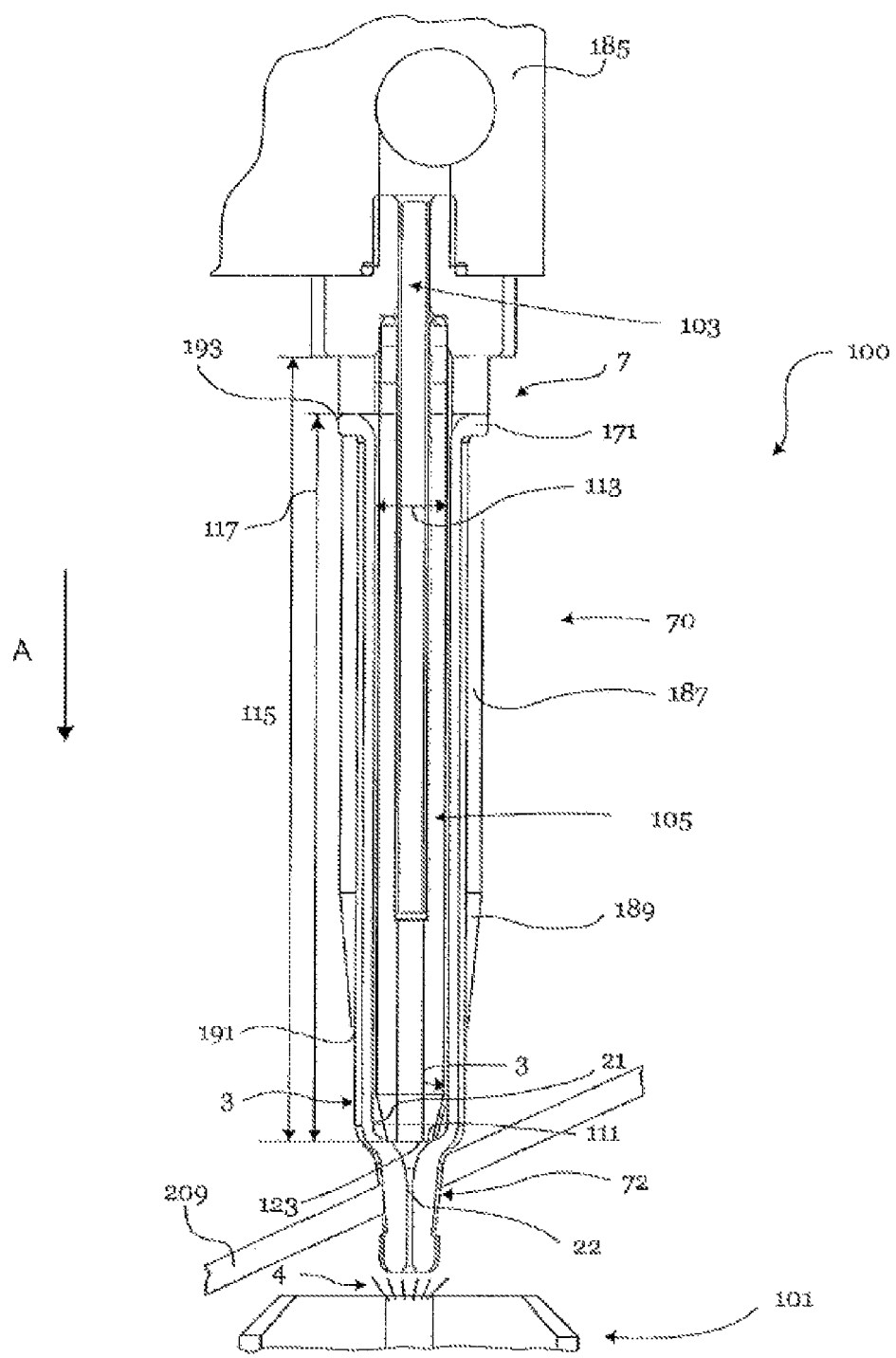
FIG. 3 a section of a plasma treatment device according to the invention.

FIG. 3 shows a section of a plasma treatment device 100 for glass syringe bodies 70 of hypodermic pre-filled glass syringes 7 in a side view. The plasma treatment device 100 comprises a support frame 185 on which at least one gripper 187 for gripping or holding a glass syringe body 70 of a hypodermic pre-filled glass syringe 7 is arranged. When viewed in the axial direction A, the gripper 187 extends approximately over three quarters of the complete longitudinal extent of the glass syringe body 70. However, the gripper 187 may also extend, for example, over 15%, 30%, 45%, 60% or even between 80% or 100% of the complete longitudinal extent of the glass syringe body 70 in the axial direction A. The gripper has a substantially constant cross-sectional shape, wherein an elongated chamfer 189 is formed over the entire circumference of the gripper 187 at the end facing away from the support frame 185. The gripper 187 has a substantially cylindrical shape, wherein a slot 191 for laterally inserting a glass syringe body 70 is provided substantially along the entire longitudinal extent of the gripper, i.e. in the axial direction A in FIG. 3. In the assembled state of the glass syringe body 70 in the gripper 187, the latter grips the glass syringe body 70 in a clamp-like manner, wherein an inner diameter of the gripper 187 approximately corresponds to the outer diameter of the glass syringe body 70, it being clear that the inner diameter of the gripper 187 should not be smaller than the outer diameter of the glass syringe body 70. It is however possible to provide an interference fit between the glass syringe body 70 and the gripper 187. Furthermore, the gripper 187 has, near the support frame 185, two grooves 193 which extend perpendicularly to the axial direction A and into which the flange section 177 of the glass syringe body 70 is to be inserted. As can be seen in particular in FIG. 3, the dimensioning of the slots 193 is selected such that the flange section 171 is suitably accommodated. One slot 193 each is introduced into the gripper 187 on both sides with respect to the glass syringe body 70.

Arranged below the glass syringe body 70 is an atmospheric-plasma pressure source 101 of the plasma treatment device 100 for providing plasma for treating an inner surface 21 of the glass syringe body 70, wherein a plasma beam directed into the syringe interior is indicated by reference numeral 4. The atmospheric-pressure plasma source 101 is explained in more detail (below) with reference to FIG. 5.

A negative pressure source 103 for providing a negative pressure of less than atmospheric pressure may be arranged on the support frame 185 itself. The atmospheric pressure source 101 and the negative pressure source 103 can be arranged opposite each other in relation to the syringe cone 72 of the glass syringe body 70 so that the negative pressure for the treatment according to the invention of at least a partial surface 22 of the inner surface 21 of the glass syringe body 70 can be carried out in the syringe cone 72. The negative pressure source 103 can also be mounted, for example, at a position other than on the support frame 185, wherein at least one applicator, such as a suction mandrel 105 of the negative pressure source 103, must be arranged according to the invention opposite the atmospheric-pressure plasma source 101 in relation to the syringe cone 72. As shown in FIG. 3, the negative pressure source 103 has a suction mandrel 105 with an outer diameter less than or equal to a plunger chamber inner diameter 113 of the glass syringe body 70 so that it can be brought into the treatment position according to the invention. It can also be seen in FIG. 3 that the suction mandrel 105 has an insertion length 115 along which the outer diameter is smaller than the plunger chamber inner diameter 113 of the glass syringe body 70. In FIG. 3, the suction mandrel 105 is inserted up to contact with a bottom surface 111 of the plunger chamber 107. In other words, a front end 123 of the suction mandrel 105 is pushed into the plunger chamber to such an extent that the front end 123 rests on the bottom surface 111 of the plunger chamber 107. The presence of a sealing means, such as a sealing ring 119 and/or a sealing hose (not shown), which is to be arranged, for example, at the front end 123 of the suction mandrel 105, may be advantageous in order to be brought into sealing contact with the inner side 109 and/or the bottom surface 111 of the plunger chamber 107.

Figure 4:
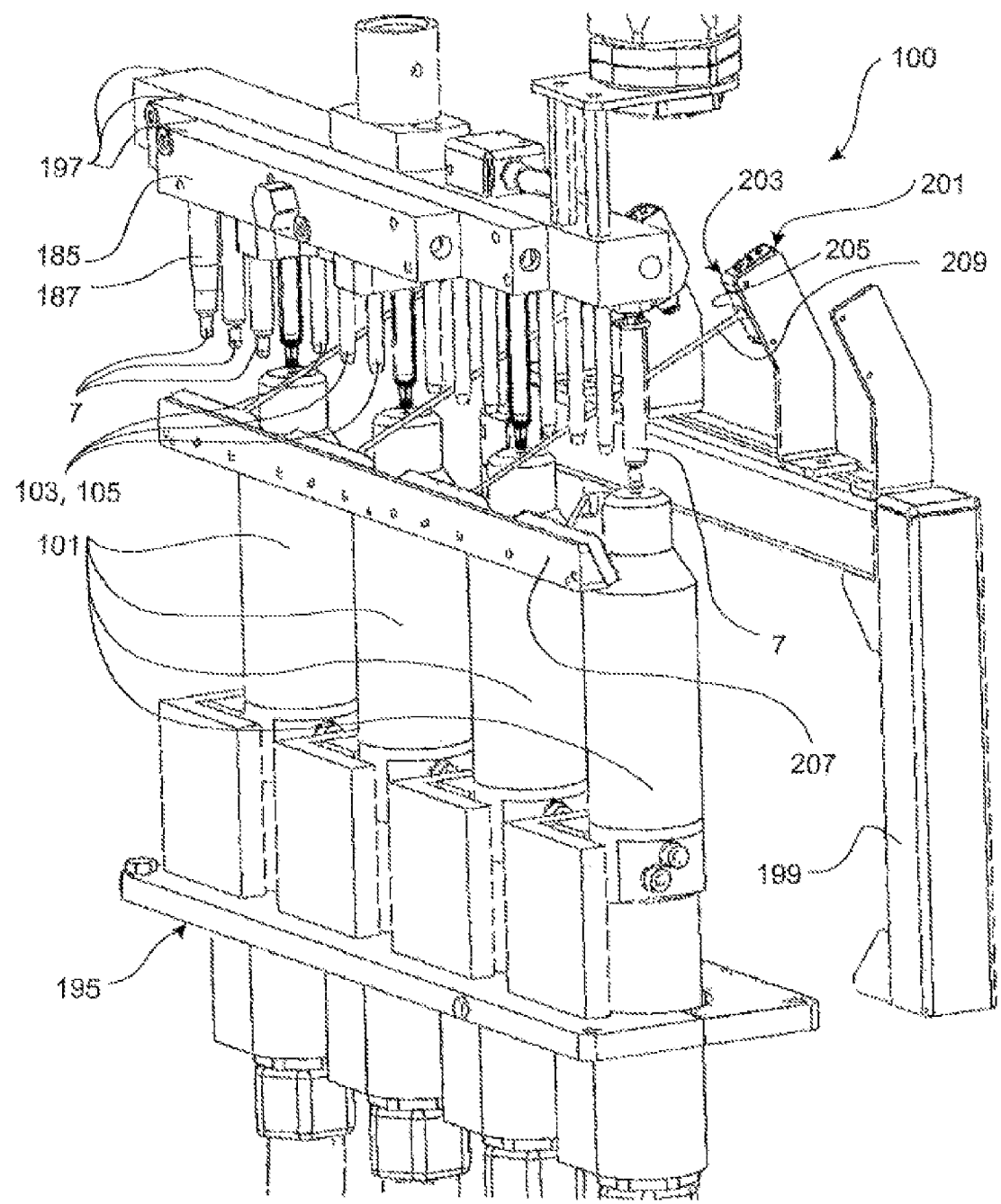
FIG. 4 an exemplary embodiment of a plasma treatment device according to the invention.

FIG. 4 shows an exemplary embodiment of a plasma treatment device 100 according to the invention. The following description explains only the components that were not already explained with reference to the previous FIGS. 1 to 3. The exemplary plasma treatment device 100 has a plasma source assembly 195 of four atmospheric-pressure plasma sources 101 for simultaneously or sequentially treating glass syringe bodies 70 of hypodermic pre-filled glass syringes 7. For example, at least five and, for example, at most 30 glass syringe bodies 70 of hypodermic glass syringes 7 can be attached in a holding manner to the support frame 185 which can consist, for example, of three longitudinal struts 197 mounted to one another, in order to treat them by means of the plasma treatment device 100. The plasma treatment device 100 is moreover designed such that negative pressure sources 103 or suction mandrels 105 of a common or separate negative pressure sources 103 corresponding to the number of accommodatable glass syringe bodies 70 are provided.

At least one or three identically designed (FIG. 4) sensor devices 201 are attached to a stand 199, which may, for example, be designed like a door frame or archway, and are used to detect whether a glass syringe body 70 is located in a gripper 187 of the support frame 185. Based on this knowledge, the atmospheric-pressure plasma source 101 and the negative pressure source 103 by means of which the respective glass syringe body 70 can be treated can then be controlled. For example, the sensor device 201 is designed as a laser device 203 and has a laser beam generator 205 attached to the stand 199 and a reflection device 207, for example a mirror device, for reflecting a laser beam 209 generated by the laser device 205. It is clear that other sensor devices 201 which are capable of detecting whether a glass syringe body 70 is in a respective holder 187 of the support frame 185 are conceivable.

Figure 5:
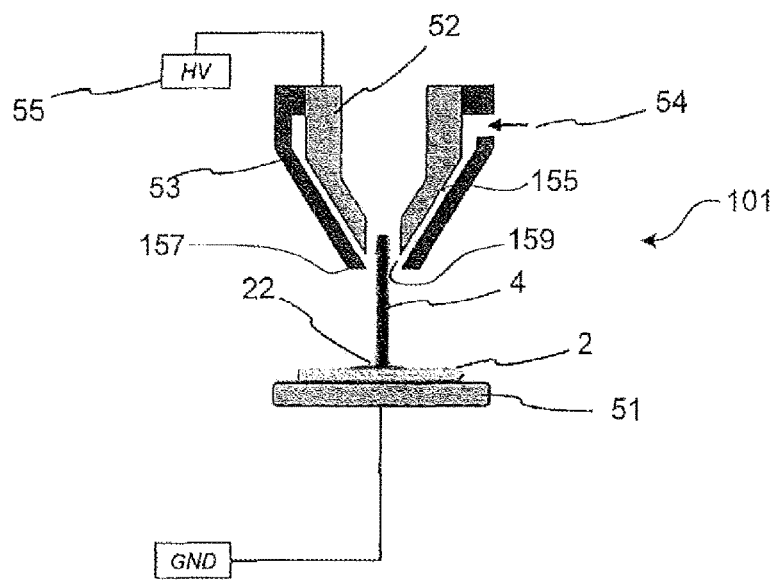
FIG. 5 an exemplary embodiment of a plasma source.

Explained in more detail with reference to FIG. 5 is a plasma source which is suitable for carrying out the above-described coating method and is designed as an atmospheric-pressure plasma source 101 by way of example. The atmospheric-pressure plasma source 101 comprises a high-voltage electrode 52 surrounded by an insulator 53. The high-voltage electrode 52 is designed as a hollow body and may, for example, be cylindrical or conical. The insulating body 53 is spaced apart from the high-voltage electrode 52. In this way, a working gas, which can be supplied via a gas supply 54, can be introduced into the intermediate space 155 between the high-voltage electrode 52 and the insulating body 53. The working gas leaves the high-voltage electrode 52 via its substrate-side orifice 157, which is designed to be funnel-like and has a longitudinally decreasing cross-section and defines an outlet opening 159 via which the working gas can leave the orifice 157.

Opposite the orifice 157 is arranged a counter electrode 51, which can optionally be provided with a dielectric coating. This ensures that a dielectrically impeded discharge is triggered between the high-voltage electrode 52 and the counter electrode 51 in every case. If the substrate itself contains or consists of a dielectric or an insulator, the dielectric coating of the counter electrode 51 can also be omitted.

During operation of the device, a working gas, for example argon, is supplied via the gas supply 54. A high-frequency alternating voltage, which is generated with a high-voltage source 55, is applied to the high-voltage electrode 52. In some embodiments of the invention, the amplitude of the applied high voltage may be between about 2 kV to about 10 kV or between about 5 kV and about 8 kV. The high voltage can be applied as a sinusoidal alternating voltage or in the form of individual high-voltage pulses. The pulse repetition frequency or alternating voltage frequency may be between about 10 Hz and about 30 kHz. The power converted in the plasma 4 can be determined by means of a measuring capacitor which integrates the transferred charge carriers of a discharge cycle. The power thus determined may be between about 0.5 watts and about 5 watts or between about 1 watt and about 3 watts.

The plasma beam produced in this way has a diameter of about 0.15 mm to about 0.5 mm. When impinging on an exemplary component 2, the root point expands so that the partial surface 22 can be larger than the diameter of the plasma beam 4. If the partial surface 22 is larger than the beam spot resulting from the geometry of the plasma source, a larger partial surface 22 can be treated by sequential treatment with the plasma 4 by displacing the component 2 or the counter electrode 51 with the component 2 arranged thereon. The distance of the beam outlet from the surface to be treated may be between about 3 mm and about 8 mm.

The elipsometrically determined layer thickness reduction of the partial surface 22 by the plasma treatment is explained with reference to FIG. 6. The treatment time with the plasma beam 4 explained with reference to FIG. 5 is plotted on the abscissa and the elipsometrically determined layer thickness is plotted on the ordinate.

Figure 6:
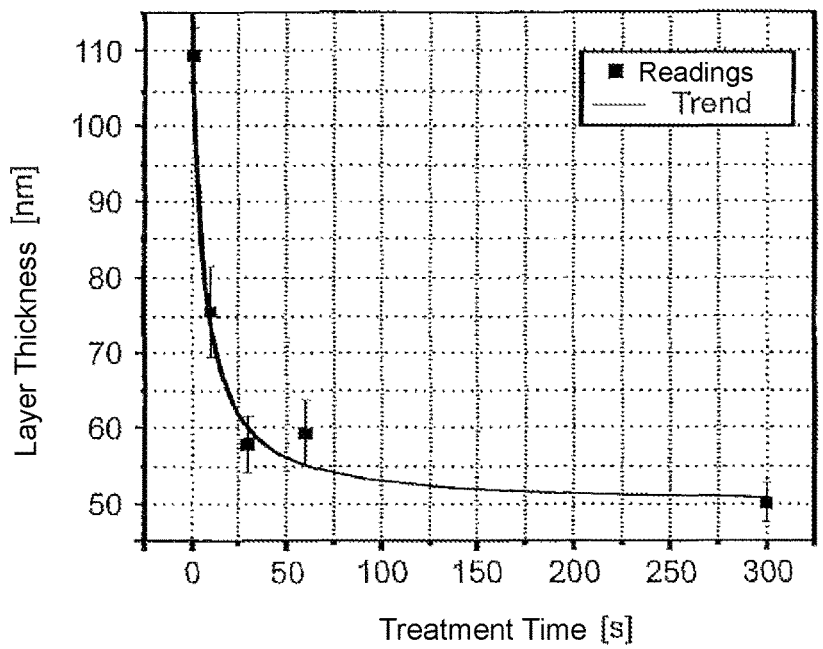
FIG. 6 a diagram of an exemplary layer thickness reduction over the treatment time.

As FIG. 6 shows, the layer thickness before the action of the plasma is 110 nm. After an exposure time of approximately 10 seconds, the layer thickness is already reduced to about 75 nm. After 30's, the layer thickness is about 57 nm. With a very long treatment time of 300 seconds, the layer thickness decreases to about 50 nm. The layer thickness shows an asymptotic curve with the treatment time. The measured values shown in FIG. 6 suggest that the layer thickness does not fall below 50 nm even with a longer treatment time.

FIG. 6 thus shows that the plasma treatment of the coating according to the invention does not achieve a complete removal of the coating. Nevertheless, the chemical composition and/or the bonding conditions of the constituents within the coating changes as explained in more detail below. This is accompanied by a change in wetting behavior. The second partial surface 22 treated with the plasma is no longer hydrophobic as originally but hydrophilic, so that the partial surface 22 is suitable after the action of the plasma 4 for being joined by means of an adhesive connection or coated again with another coating material.

The measured values shown in FIG. 6 were determined on the basis of a coating 3 obtained by bake-on siliconization. For this purpose, an emulsion of silicone oil and water is applied and subsequently baked onto the surface of the component 2 by a heat treatment. The table below shows the element inventory of the coating 3 before the action of the plasma after 1 second, 10 seconds, 30 seconds, 60 seconds and after 300 seconds. All measured values were obtained by photoelectron spectroscopy. Monochromatic x-radiation is irradiated onto the surface of the coating 3 and the kinetic energy of the photoelectrons is determined. The respective element can be determined from the kinetic energy, and the intensity of the photoelectrons indicates the relative proportions in the coating 3.

TABLE 1

Elemental inventory of the coating

| Element | 0 s [Atomic %] | 1 s [Atomic %] | 10 s [Atomic %] | 30 s [Atomic %] | 60 s [Atomic %] | 300 s [Atomic %] |
|---|---|---|---|---|---|---|
| Oxygen (O) | 39.1 | 56.2 | 60.4 | 67 | 66.96 | 66.96 |
| Carbon (C) | 35.8 | 18.93 | 13.9 | 5.6 | 4.14 | 3.63 |
| Silicon (Si) | 25.1 | 24.85 | 25.7 | 27.4 | 28.68 | 29.28 |
| Remainder | — | — | — | — | 0.27 | 0.13 |

The measurements were obtained after the action of an atmospheric-pressure plasma beam 4, which is obtainable, for example, with the device according to FIG. 5, with atmospheric air as working gas. As the measured values shown above show, the carbon content of the coating decreases rapidly as the exposure time to the plasma increases. This is attributable to the fact that the methyl groups contained in the silicone separate and are transported away by the gas stream of the working gas of the plasma 4.

In order to increase the needle holding force between the injection needle 73 and the pre-filled glass syringe 7, in particular in order to ensure strength values within the scope of DIN ISO 7864, the method step according to the invention of placing a negative pressure source 103 opposite the atmospheric-pressure plasma source 101 in relation to the syringe cone 72 is used. After being treated with plasma 4 with simultaneous application of negative pressure by the negative pressure source 103, the coating of a partial surface 22 is treated in such a way that subsequent adhesion of an adhesive to be applied to the partial surface 22 is significantly enhanced in order to thus increase the holding force between the cannula 76 or the injection needle 73 and the pre-filled glass syringe 7.

Figure 7:
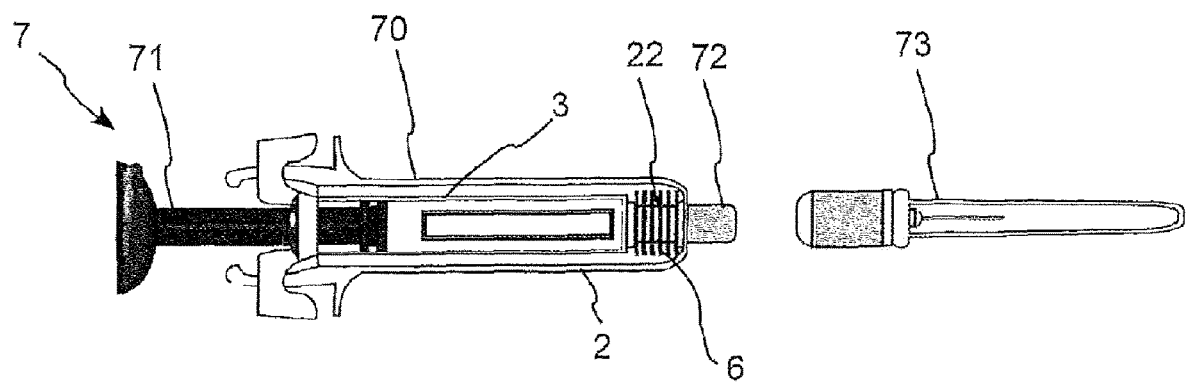
FIG. 7 a further embodiment of a hypodermic pre-filled glass syringe according to the invention.

FIG. 7 shows a pre-filled syringe, which is designed as a pre-filled glass syringe 7 by way of example as a further exemplary embodiment of the invention. The pre-filled glass syringe 7 has an approximately cylindrical syringe body 70. Pre-filled glass syringes 7 of the type shown serve as packaging of the medicine contained therein in the production plant so that the medicine can be given to the doctor or patient in an immediately ready-for-use form.

In order to produce (not shown) the pre-filled glass syringe 7 illustrated in FIG. 7, the syringe body 70 is first produced from a glass tube. For this purpose, the glass tube is cut, heated and shaped in accordance with the desired shape.

In the next method step, at least the inner side is treated, for example sprayed, with an emulsion of a solvent and layer-forming substances and subsequently treated in an oven or heating cabinet. This causes a majority of the solvent present in the emulsion to evaporate. At the same time, the silicone contained as a layer-forming substance is covalently bonded to the glass so that a coating 3 which contains or consists of polysiloxane is formed on the inner side. The heat treatment prevents the silicone from undesirably transferring into the medicine during later filling, storage and use of the pre-filled glass syringe 7. At the same time, the siliconization allows easy sliding of the plunger 7 so that the handling of the pre-filled glass syringe 7 is facilitated.

In the illustrated embodiment, a cone 72, which is provided for receiving the injection needle 73, is glued to the end of the syringe body 70 opposite the plunger 71. In other embodiments of the invention, the injection needle 73 can also be glued directly into the syringe body 70 so that the cone 72 can also be omitted, or the cone 72 is alternatively made of one piece together with the glass syringe body 70.

Since the coating 3 also covers the partial surface 22 provided for receiving the cone 72, the adhesive strength of an adhesive connection 6 is reduced. This can go so far that the cone 72 already falls out of the syringe body 70 during transport or storage and the contents of the pre-filled glass syringe 7 leaks out.

According to the invention, it is therefore proposed to treat the partial surface 22 with an atmospheric-pressure plasma in the manner described above and to thereby not completely remove the coating 3 but to inactivate it to such an extent that the adhesive connection 6 can be reliably filled. This is done according to the invention by the application of a negative pressure source 103 which is arranged in relation to the syringe cone 72 in the axial direction A opposite the atmospheric-pressure plasma source 101 and provides a negative pressure of less than atmospheric pressure. By changing the element inventory and/or the bonding conditions of the constituents, the hydrophobic coating 3 in the partial surface 22 can become hydrophilic in order to significantly improve the adhesive strength of the adhesive bond 6 or to provide needle holding forces in the axial direction A which satisfy the requirements of DIN ISO 7864.

Figure 8:
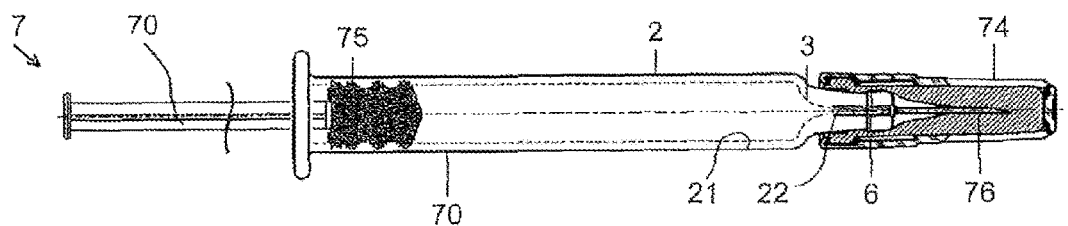
FIG. 8 a further embodiment of a hypodermic pre-filled glass syringe according to the invention.

FIG. 8 shows a pre-filled syringe, which can, for example, also be designed as a pre-filled glass syringe 7, and the principal function of which was already explained with reference to the previous embodiments. The same components are provided with the same reference numerals so that the description below is limited to the essential differences.

In order to produce the pre-filled glass syringe 7 (staked-in-needle syringe) illustrated in FIG. 8, the syringe body 70 is first produced from a glass tube. For this purpose, the glass tube is cut, heated and shaped in accordance with the desired shape. However, the syringe body 70 may also be made of plastic (not shown). Plastic syringes are produced by known production methods, e.g. injection molding.

In the next method step, at least the inner side of the syringe body 70 is sprayed with an emulsion of a solvent and layer-forming substances and subsequently treated in an oven, for example a tunnel furnace, or heating cabinet. This causes a majority of the solvent present in the emulsion to evaporate. At the same time, the silicone contained as a layer-forming substance is for the most part covalently bonded to the glass so that a coating 3 which contains or consists of polysiloxane and/or polydimethylsiloxane is formed on the inner side, i.e. on the inner surface 21 including the partial surface 22. The heat treatment prevents the silicone from undesirably transferring into the medicine during later filling, storage and use of the pre-filled glass syringe 7. At the same time, the siliconization allows easy sliding of the plunger plug 75 so that the handling of the pre-filled glass syringe 7 or application of the medicine is facilitated or made possible in the first place.

In the embodiment shown, a cannula 76 is glued to the end of the syringe body 70 opposite the plunger plug 75. Since the coating 3 also covers the partial surface 22 provided for receiving the cannula 76, the adhesive strength of an adhesive connection 6 is reduced. This can go so far that the cannula 76 already falls out of the syringe body 70 during transport or storage and the content of the pre-filled glass syringe 7 leaks out.

According to the invention, it is therefore proposed to treat the partial surface 22 according to the above-described coating method according to the invention with an atmospheric-pressure plasma source 101 and a negative pressure source 103 which are arranged according to the invention opposite each other in the axial direction A with respect to the syringe cone 72, and wherein the negative pressure source 103 provides a negative pressure of less than atmospheric pressure in particular in the syringe cone 72 in order to enhance the adhesion capability of adhesive on the partial surface 22 of the inner surface 21 of the pre-filled glass syringe 7 so that a holding force between the cannula or injection needle 73 and the glass syringe 7 according to DIN ISO 7864 is achieved. By changing the element inventory and/or the bonding conditions of the constituents, the hydrophobic coating 3 in the second partial surface can become hydrophilic and thus improve the adhesive strength of the adhesive connection 6.

After the cannula 76 has been glued into the syringe body 70, the pre-filled glass syringe 7 is prepared for filling in a manner known per se, i.e. cleaned, sterilized and packaged. The needle protection part 74 is also seated on the cannula 76 in the process. The syringe prepared in this way for filling is then delivered to the manufacturer of the medicine in order to be filled.

The features disclosed in the above description, the figures and the claims may be important both individually and in any combination for realizing the invention in the various embodiments.

LIST OF REFERENCE NUMERALS

2 Component
3 Coating
4 Plasma
6 Adhesive connection
7 Pre-filled glass syringe
21 Inner surface
22 Partial surface
51 Counter electrode
52 High-voltage electrode
53 Insulator
54 Gas supply
55 High-voltage source
70 Glass syringe body
71 Plunger
72 Syringe cone
73 Injection needle
74 Needle protection part
75 Plunger plug
76 Cannula
100 Plasma treatment device
101 Atmospheric-pressure plasma source
103 Negative pressure source
105 Suction mandrel
107 Plunger chamber
109 Inner side
111 Bottom surface
113 Plunger chamber inner diameter
115 Insertion length
119 Sealing ring
123 Front end
155 Intermediate space
157 Orifice
159 Outlet opening
171 Flange section
173 Flange end
175 Plunger section
177 Funnel section
179 Passage or end channel
181 Syringe cone end
183 Flange web
185 Support frame
187 Gripper
189 Chamfer
191, 193 Slot
197 Longitudinal strut
199 Stand
201 Sensor device
203 Laser device
205 Laser beam generator
207 Reflection device
209 Laser beam
A Axial direction
M Center axis

The invention claimed is:

1. A method for forming a coating on an inner surface of a glass syringe body comprising the steps of:
applying at least one emulsion and/or one solution containing at least one layer-forming substance to at least one inner surface of the glass syringe body, said glass syringe body having an axial direction (A) and comprising a syringe cone positioned at a first end of the glass syringe body along the axial direction (A);
generating plasma using an atmospheric-pressure plasma source positioned in front of the first end of the glass syringe body;
subsequently exposing at least a partial surface of an inner surface of the syringe cone to the plasma, wherein the plasma is introduced into the glass syringe body from the atmospheric-pressure plasma source through the syringe cone;
simultaneous with exposing at least the partial surface of the inner surface of the syringe cone to the plasma, applying a negative pressure of less than atmospheric pressure to a second end of the glass syringe body, wherein the negative pressure is provided by a negative pressure source arranged at the second end of the glass syringe body, and wherein the second end of the glass syringe body is opposite to the first end of the glass syringe body in the axial direction (A).

2. The method according to claim 1, wherein a suction mandrel of the negative pressure source is introduced into a plunger chamber of the glass syringe body.

3. The method according to claim 2, wherein the suction mandrel is brought into a sealing contact with an inner side and/or a bottom surface of the plunger chamber.

4. Then method according to claim 1, wherein the coating comprises a carbon content which decreases to less than about 80% of the initial value before the plasma treatment.

5. The method according to claim 1, wherein the layer thickness of the coating in at least the partial surface of the inner surface before the action of the plasma is between about 20 nm and about 100 nm and decreases in the partial surface by more than about 20% as a result of the plasma treatment.

6. The method according to claim 1, wherein a layer thickness of more than about 70% remains after the plasma treatment in the partial surface.

7. The method according to claim 1, wherein the emulsion and/or the solution comprises at least one silicone oil and optionally water, and/or the coating contains at least carbon and oxygen and hydrogen and silicon, and/or the coating contains at least one poly(-organo)-siloxane.

8. The method according to claim 1, wherein the partial surface of the inner surface of the syringe cone is hydrophobic before the plasma treatment and hydrophilic after the plasma treatment.

9. The method according to claim 1, wherein the plasma comprises an active gas, wherein the active gas optionally comprises oxygen or synthetic air or atmospheric air.

10. The method according to claim 1, wherein the plasma acts for about 0.4 to about 5 seconds, and/or an atmospheric-pressure plasma generated with a dielectrically impeded discharge is used, and/or the plasma comprises an inert gas, and/or that the plasma is formed as a plasma beam or plasma jet which acts at least on the partial surface of the inner surface of the syringe cone, and/or the plasma acts while the negative pressure is provided.

11. The method according to claim 1, further comprising connecting an injection needle to the glass syringe body along a joint by means of an adhesive, wherein the joint comprises the partial surface of the inner surface of the syringe cone.

12. The method according to claim 11, wherein the adhesive is selected from an acrylate and/or a polyurethane and/or an epoxy resin and/or a cyanoacrylate.

\* \* \* \* \*